(12) United States Patent
Ionescu et al.

(10) Patent No.: US 8,481,715 B2
(45) Date of Patent: *Jul. 9, 2013

(54) METHODS FOR ISOLATING CRYSTALLINE FORM I OF 5-AZACYTIDINE

(75) Inventors: Dumitru Ionescu, Ann Arbor, MI (US); Peter Blumbergs, Royal Oak, MI (US); Gary L. Silvey, Overland Park, KS (US)

(73) Assignee: Pharmion LLC, Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/489,307

(22) Filed: Jun. 5, 2012

(65) Prior Publication Data

US 2012/0245342 A1    Sep. 27, 2012

Related U.S. Application Data

(60) Division of application No. 12/729,116, filed on Mar. 22, 2010, now Pat. No. 8,211,862, which is a continuation of application No. 11/198,550, filed on Aug. 5, 2005, now Pat. No. 7,700,770, which is a division of application No. 10/390,530, filed on Mar. 17, 2003, now Pat. No. 6,943,249.

(51) Int. Cl.
*C07H 19/12* (2006.01)

(52) U.S. Cl.
USPC ..................................................... 536/28.3

(58) Field of Classification Search
None
See application file for complete search history.

(56) References Cited

U.S. PATENT DOCUMENTS

| | | |
|---|---|---|
| 3,350,388 A | 10/1967 | Sorm et al. |
| 3,817,980 A | 6/1974 | Vorbruggen et al. |
| 3,891,623 A | 6/1975 | Vorbruggen et al. |
| 4,082,911 A | 4/1978 | Vorbruggen |
| 4,209,613 A | 6/1980 | Vorbruggen |
| 5,700,640 A | 12/1997 | Voss et al. |
| 5,985,864 A | 11/1999 | Imai et al. |
| 6,642,206 B2 | 11/2003 | Ramasamy et al. |
| 6,723,728 B2 | 4/2004 | Hu et al. |
| 6,753,426 B2 | 6/2004 | Zhang et al. |
| 6,887,855 B2 | 5/2005 | Ionescu et al. |
| 6,943,249 B2 * | 9/2005 | Ionescu et al. ............... 544/212 |
| 7,038,038 B2 | 5/2006 | Ionescu et al. |
| 7,078,518 B2 | 7/2006 | Ionescu et al. |
| 7,084,268 B1 | 8/2006 | Chiba et al. |
| 7,132,552 B2 | 11/2006 | Dolitzky et al. |
| 7,189,740 B2 | 3/2007 | Zeldis |
| 7,192,781 B2 | 3/2007 | Luna et al. |
| 7,642,247 B2 | 1/2010 | Daifuku et al. |
| 7,700,770 B2 | 4/2010 | Ionescu et al. |
| 7,759,481 B2 | 7/2010 | Gavenda et al. |
| 7,772,199 B2 | 8/2010 | Ionescu et al. |
| 7,858,774 B2 | 12/2010 | Ionescu et al. |
| 8,058,424 B2 | 11/2011 | Ionescu et al. |
| 8,211,862 B2 | 7/2012 | Ionescu et al. |
| 2004/0162263 A1 | 8/2004 | Sands et al. |
| 2004/0186065 A1 | 9/2004 | Ionescu et al. |
| 2005/0075508 A1 | 4/2005 | Fukae et al. |
| 2006/0063735 A1 | 3/2006 | Redkar et al. |
| 2006/0069060 A1 | 3/2006 | Redkar et al. |
| 2006/0074046 A1 | 4/2006 | Redkar et al. |
| 2006/0128654 A1 | 6/2006 | Tang et al. |
| 2007/0190022 A1 | 8/2007 | Bacopoulos et al. |
| 2008/0057086 A1 | 3/2008 | Etter et al. |
| 2008/0182806 A1 | 7/2008 | Pizzorno |
| 2009/0286752 A1 | 11/2009 | Etter et al. |
| 2010/0035354 A1 | 2/2010 | Bigatti et al. |
| 2010/0036112 A1 | 2/2010 | Henschke et al. |
| 2010/0062992 A1 | 3/2010 | Redkar et al. |
| 2010/0210833 A1 | 8/2010 | Jungmann et al. |
| 2010/0292180 A1 | 11/2010 | Ionescu et al. |
| 2010/0298253 A1 | 11/2010 | Ionescu et al. |
| 2010/0311683 A1 | 12/2010 | Beach et al. |
| 2011/0042247 A1 | 2/2011 | Kocherlakota et al. |
| 2011/0092694 A1 | 4/2011 | Ionescu et al. |
| 2011/0201800 A1 | 8/2011 | Cherukupally et al. |
| 2011/0245485 A1 | 10/2011 | De Ferra et al. |
| 2012/0029181 A1 | 2/2012 | Ionescu et al. |

FOREIGN PATENT DOCUMENTS

| | | |
|---|---|---|
| CZ | 114716 | 11/1964 |
| CZ | 116297 | 4/1965 |
| DE | 1922702 | 11/1969 |

(Continued)

OTHER PUBLICATIONS

U.S. Appl. No. 13/587,768, filed Aug. 16, 2012, Ionescu et al.

(Continued)

*Primary Examiner* — Yong Chu
(74) *Attorney, Agent, or Firm* — Jones Day

(57) ABSTRACT

The invention includes methods for isolating crystalline Form I of 5-azacytidine substantially free of other forms, wherein 5-azacytidine is represented by the formula:

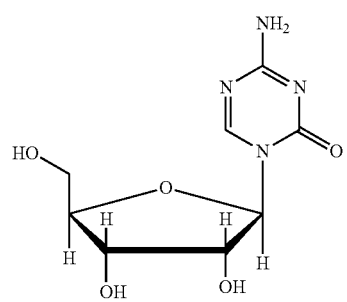

The invention also includes pharmaceutical compositions comprising Form I of 5-azacytidine.

12 Claims, No Drawings

FOREIGN PATENT DOCUMENTS

| | | |
|---|---|---|
| DE | 2012888 | 9/1971 |
| FR | 2123632 | 9/1972 |
| GB | 1227691 | 4/1971 |
| GB | 1227692 | 4/1971 |
| WO | WO 2004/082619 | 9/2004 |
| WO | WO 2006/034154 | 3/2006 |
| WO | WO 2008/088779 | 7/2008 |
| WO | WO 2009/016617 | 2/2009 |
| WO | WO 2011/014541 | 2/2011 |

OTHER PUBLICATIONS

U.S. Appl. No. 13/587,770, filed Aug. 16, 2012, Ionescu et al.
Ault, Techniques and Experiments for Organic Chemistry, 6th ed., University Science Books, 59-60 (1998).
Beers et al. (eds.), Chapter 142, Section 11, in the Merck Manual of Diagnosis and Therapy, 18th Edition, pp. 1114-1116 (2006).
Beisler et al., "Chemistry of Antitumor Triazine Nucleosides. An Improved Synthesis of Dihydro-5-Azacytidine," J. Carbohydrates Nucleosides Nucleotides, 4(5): 281-99 (1977).
Beisler et al., "Synthesis and Antitumor Activity of Dihydro-5-azacytidine, a Hydrolytically Stable Analogue of 5-Azacytidine," J. Med. Chem., 20(6): 806-12 (1977).
Beisler, "Isolation, Characterization, and Properties of a Labile Hydrolysis Product of the Antitumor Nucleoside, 5-Azacytidine," J. Med. Chem., 21(2): 204-08 (1978).
Bergy et al., "Microbiological Production of 5-Azacytidine II. Isolation and Chemical Structure," Antimicrobial Agents and Chemotherapy, 625-30 (1966).
Bond et al., "Controlling Crystal Architecture in Molecular Solids: the Supramolecular Approach," in Supramolecular Organization and Materials Design, Jones & Rao eds., Cambridge University Press, Chapter 12, pp. 391-443 (2002).
Braga et al., "Making Crystals From Crystals: a Green Route to Crystal Engineering and Polymorphism," Chemical Communications, 3635-45 (2005).
Brittain, "Polymorphism: Pharmaceutical Aspects," in Encyclopedia of Pharmaceutical Technology, 2nd Edition, vol. 3, Swarbrick & Boylan eds., pp. 2239-2249 (2002).
Byrn et al., "Drugs as Molecular Solids," in Solid-State Chemistry of Drugs, 2nd Edition, pp. 3-43 (1999).
Cabri et al., "Polymorphisms and Patent, Market, and Legal Battles: Cefdinir Case Study," Organic Process Research & Development, 11: 64-72 (2007).
Chan, K.K. et al., "5-Azacytidine Hydrolysis Kinetics Measured by High-Pressure Liquid Chromatography and 13C-NMR Spectroscopy," J. Pharm. Sci., 68(7): 807-12 (1979).
Chen et al., "Highly Efficient Regioselective Synthesis of 5'-O-lauroyl-5-azacytidine Catalyzed by Candida Antarctica Lipase B," Appl. Biochem. Biotechnol., 151: 21-28 (2008).
Day et al., "An Assessment of Lattice Energy Minimization for the Prediction of Molecular Organic Crystal Structures," Crystal Growth & Design, 4(6): 1327-40 (2004).
Dean, Analytical Chemistry Handbook, pp. 10.23-10.26 (1995).
Dintaman et al., "Inhibition of P-Glycoprotein by D-α-Tocopheryl Polyethylene Glycol 1000 Succinate (TPGS)," Pharmaceutical Research, 16(10): 1550-1556 (1999).
Dover et al., "5-Azacytidine Increases HbF Production and Reduces Anemia in Sickle Cell Disease: Dose-Response Analysis of Subcutaneous and Oral Dosage Regimens," Blood, 66(3): 527-532 (1985).
Garcia-Manero et al., "A Pilot Pharmacokinetic Study of Oral Azacitidine," Leukemia, 22: 1680-84 (2008).
Garcia-Manero et al., "Phase 1 Study of Oral Azacitidine in Myelodysplastic Syndromes, Chronic Myelomonocytic Leukemia, and Acute Myeloid Leukemia," J. Clin. Oncol., 29(18): 2521-27 (2011).
Gaubert et al., "Unnatural Enantiomers of 5-Azacytidine Analogues: Synthesis and Enzymatic Properties," Nucleosides, Nucleotides & Nucleic Acids, 20(4-7): 837-40 (2001).
Giron, "Investigations of Polymorphism and Pseudo-Polymorphism Pharmaceuticals by Combined Thermoanalytical Techniques," Journal of Thermal Analysis and Calorimetry, 64: 37-60 (2001).
Giron, "Thermal Analysis and Calorimetric Methods in the Characterisation of Polymorphs and Solvates," Thermochimica Acta, 248: 1-59 (1995).
Guillory, "Generation of Polymorphs, Hydrates, Solvates, and Amorphous Solids," in Polymorphism in Pharmaceutical Solids, pp. 183-226 (1999).
Gut et al., "Aza Analogs of Pyrimidine and Purine Bases of Nucleic Acids," in Advances in Heterocyclic Chemistry, vol. 1, Katritzky ed., pp. 189-251 (1963).
Hanka et al., "Microbiological Production of 5-Azacytidine I. Production and Biological Activity," Antimicrobial Agents and Chemotherapy, 619-24 (1966).
Hilfiker et al., in Polymorphism in the Pharmaceutical Industry, pp. 1-19, 287-308 (2006).
Jain et al., "Polymorphism in Pharmacy," Indian Drugs, 23(6): 315-29 (1986).
Jones et al., "Pharmaceutical Cocrystals: An Emerging Approach to Physical Property Enhancement," MRS Bulletin, 31: 875-79 (2006).
Khankari et al., "Pharmaceutical Hydrates," Thermochimica Acta, 248: 61-79 (1995).
Knapman, "Polymorphic Predictions: Understanding the Nature of Crystalline Compounds Can Be Critical in Drug Development and Manufacture," Modern Drug Discovery, 53-57 (2000).
Kornblith et al., "Impact of Azacytidine on the Quality of Life of Patients with Myelodysplastic Syndrome Treated in a Randomized Phase III Trial: A Cancer and Leukemia Group B Study," J. Clin Oncol., 20(10): 2441-52 (2002).
Kritz et al., "Pilot Study of 5-Azacytidine (5-AZA) and Carboplatin (CBDCA) in Patients with Relapsed/Refractory Leukemia," American Journal of Hematology, 51(2): 117-21 (1996).
Landgrebe, Organic Laboratory, 4th Edition, pp. 111-112 (1993).
Lin et al., "High Performance Liquid Chromatographic Analysis of Chemical Stability of 5-Aza-2'-deoxycytidine," J. Pharm. Sci., 70(11): 1228-32 (1981).
Morissette et al., "Elucidation of Crystal Form Diversity of the HIV Protease Inhibitor Ritonavir by High-Throughput Crystallization," Proc. Natl. Acad. Sci., 100(5): 2180-84 (2003).
New Experimental Chemistry Seminar, Basic Operation I, Japan Chemical Society, 3rd Print, pp. 318-327 (1978).
Niedballa et al., "A General Synthesis of N-Glycosides. V. Synthesis of 5-Azacytidines," J. Org. Chem., 39(25): 3672-74 (1974).
Notari et al., "Kinetics and Mechanisms of Degradation of the Antileukemic Agent 5-Azacytidine in Aqueous Solutions," J. Pharm. Sci., 64(7), 1148-57 (1975).
O'Neil et al. (eds.), The Merck Index, 13th Edition, p. 154-55 (2001).
O'Neil et al. (eds.), The Merck Index, 14th Edition, p. 150 (2006).
Piskala et al., "4-Amino-1-Beta-D-Ribofuranosyl-Triazin-2(1H)-one (5-azacytidine)," Nucleic Acid Chem., 1: 435-41 (1978).
Piskala et al., "Direct Synthesis of 5-Azapyrimidine Ribonucleosides," Nucleic Acids Research, Special Pub. No. 1: s17-20 (1975).
Piskala et al., "Nucleic Acids Components and Their Analogues. LI. Synthesis of 1-Glycosyl Derivatives of 5-Azauracil and 5-Azacytosine," Collect. Czech. Chem. Commun., 29: 2060-76 (1964).
Seddon, "Pseudopolymorph: A Polemic," Crystal Growth & Design, 4(6): 1087 (2004).
Silverman et al., "Randomized Controlled Trial of Azacitidine in Patients with the Myelodysplastic Syndrome: A Study of the Cancer and Leukemia Group B," J. Clin. Oncol., 20(10): 2429-40 (2002).
Skikne et al., "A Phase I, Open-Label, Dose-Escalation Study to Evaluate the Safety, Pharmacokinetics, and Pharmacodynamics of Oral Azacitidine in Subjects with Myelodysplastic Syndromes (MDS) or Acute Myelogenous Leukemia (AML)," Journal of Clinical Oncology (May 20, 2008 Supplement), 2008 ASCO Annual Meeting Proceedings (Meeting Date: May 30-Jun. 3, 2008), Part I, 2008, 26(15S), poster # 7091 (2008).
Stavchansky et al., "Bioavailability in Tablet Technology," in Pharmaceutical Dosage Forms, Tablets, 2nd Edition, Revised and Expanded, vol. 2 of 3, Lieberman et al. eds., pp. 462-472 (1990).

Stoltz et al., "Development of an Oral Dosage Form of Azacitidine: Overcoming Challenges in Chemistry, Formulation, and Bioavailability," Blood, 48th ASH Annual Meeting (Meeting Date: Dec. 9-12, 2006), 108, poster # 4850 (2006).

Vippagunta et al., "Crystalline Solids," Advanced Drug Delivery Reviews, 48: 3-26 (2001).

Vogler et al., "5-Azacytidine (NSC 102816): A New Drug for the Treatment of Myeloblastic Leukemia," Blood, 48(3): 331-37 (1976).

Vorbruggen et al., "A New Simplified Nucleoside Synthesis," Chem. Ber., 114: 1279-86 (1981).

Vorbruggen et al., "Nucleoside Synthesis with Trimethylsilyl Triflate and Perchlorate as Catalysts," Chem. Ber., 114: 1234-55 (1981).

Vorbruggen et al., in Organic Reactions, vol. 55, 100 (L.A. Paquette ed., John Wiley & Sons, New York, 2000).

Ward et al., "An Oral Dosage Formulation of Azacitidine: A Pilot Pharmacokinetic Study," Journal of Clinical Oncology (Jun. 20, 2007 Supplement), 2007 ASCO Annual Meeting Proceedings (Meeting Date: Jun. 1-5, 2007), Part I, 25(18S), poster # 7084 (2007).

Winkley et al., "Direct Glycosylation of 1,3,5-Triazinones. A New Approach to the Synthesis of the Nucleoside Antibiotic 5-Azacytidine (4-Amino-1-β-D-ribofuranosyl-1,3,5-triazin-2-one) and Related Derivatives," J. Org. Chem., 35(2): 491-95 (1970).

Wittenburg et al., "A New Synthesis of Nucleosides," Zeitschrift fur Chemie, 4: 303-04 (1964) (with English translation).

Zaitseva et al., "Convergent Syntheses and Cytostatic Properties of 2-Chloro-2'-Deoxy-2'-Fluoroadenosine and its N7-Isomer," Bioorg. & Med. Chem. Lett., 5(24): 2999-3002 (1995).

Ziemba et al., "Development of Oral Demethylating Agents for the Treatment of Myelodysplastic Syndromes," American Association of Cancer Research, 100th Annual Meeting, Apr. 18-22, Abstract #3369 (2009).

Office Action dated Aug. 1, 2011 in U.S. Appl. No. 12/466,213.

Opposition Brief dated Sep. 3, 2007 in Chile Application No. 2267-2005 (with English translation).

Non-Final Office Action dated Sep. 23, 2011 in U.S. Appl. No. 12/787,214.

Notice of Allowability dated May 4, 2012 in U.S. Appl. No. 12/729,116.

Notice of Allowance dated Sep. 20, 2011 in U.S. Appl. No. 12/729,116.

Final Office Action dated Mar. 6, 2012 in U.S. Appl. No. 12/787,214.

Communication Pursuant to Rule 114(2) EPC, enclosing a third party observation, issued by the EPO on Jan. 31, 2013 for European Application No. 10151392.7.

* cited by examiner

METHODS FOR ISOLATING CRYSTALLINE FORM I OF 5-AZACYTIDINE

This application is a divisional of U.S. patent application Ser. No. 12/729,116, filed Mar. 22, 2010, entitled Pharmaceutical Compositions Comprising Crystal Forms of 5-Azacytidine (now U.S. Pat. No. 8,211,862); which is a continuation of U.S. patent application Ser. No. 11/198,550, filed Aug. 5, 2005, entitled Methods for Isolating Crystalline Form I of 5-Azacytidine (now U.S. Pat. No. 7,700,770); which is a divisional of U.S. patent application Ser. No. 10/390,530, filed Mar. 17, 2003, entitled Methods for Isolating Crystalline Form I of 5-Azacytidine (now U.S. Pat. No. 6,943,249).

FIELD OF THE INVENTION

The invention relates to the isolation of crystalline polymorphic Form I of 5-azacytidine (also known as azacitidine and 4-amino-1-β-D-ribofuranosyl-S-triazin-2(1H -one). 5-azacytidine may be used in the treatment of disease, including the treatment of myelodysplastic syndromes (MDS).

BACKGROUND OF THE INVENTION

Polymorphs exist as two or more crystalline phases that have different arrangements and/or different conformations of the molecule in a crystal lattice. When a solvent molecule(s) is contained within the crystal lattice the resulting crystal is called a pseudopolymorph, or solvate. If the solvent molecule(s) within the crystal structure is a water molecule, then the pseudopolymorph/solvate is called a hydrate. The polymorphic and pseudopolymorphic solids display different physical properties, including those due to packing, and various thermodynamic, spectroscopic, interfacial and mechanical properties (See H. Brittain, Polymorphism in Pharmaceutical Solids, Marcel Dekker, New York, N.Y., 1999, pp. 1-2). Polymorphic and pseudopolymorphic forms of the drug substance (also known as the "active pharmaceutical ingredient" (API)), as administered by itself or formulated as a drug product (also known as the final or finished dosage form, or as the pharmaceutical composition) are well known and may affect, for example, the solubility, stability, flowability, fractability, and compressibility of drug substances and the safety and efficacy of drug products, (see, e.g., Knapman, K Modern Drug Discoveries, March 2000: 53).

5-azacytidine (also known as azacitidine and 4-amino-1-β-D-ribofuranosyl-S-triazin-2(1H)-one; Nation Service Center designation NSC-102816; CAS Registry Number 320-67-2) has undergone NCI-sponsored trials for the treatment of myelodysplastic syndromes (MDS). See Kornblith et al., J. Clin. Oncol. 20(10): 2441-2452 (2002) and Silverman et al., J. Clin. Oncol. 20(10): 2429-2440 (2002). 5-azacytidine may be defined as having a formula of $C_8H_{12}N_4O_5$, a molecular weight of 244.20 and a structure of:

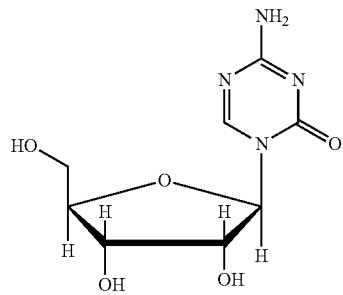

In the United States patent application entitled "Forms of 5-azacytidine," Ser. No. 10/390,578, filed Mar. 17, 2003 and incorporated herein by reference in its entirety, eight different polymorphic and pseudopolymorphic forms of 5-azacytidine (Forms I-VIII), in addition to an amorphous form, are described. Forms I-VIII each have characteristic X-Ray Powder Diffraction (XRPD) patterns and are easily distinguished from one another using XRPD.

5-azacytidine drug substance used in the previous clinical trials has typically been synthesized from 5-azacytosine and 1,2,3,5,-tetra-O-acetyl-β-D-ribofuranose by the method presented in Example 1. The last step of this method is a recrystallization of the crude synthesis product from a methanol/DMSO co-solvent system. Specifically, the crude synthesis product is dissolved in DMSO (preheated to about 90° C.), and then methanol is added to the DMSO solution. The product is collected by vacuum filtration and allowed to air dry.

In Ser. No. 10/390,578 (supra), it is demonstrated that this prior art method for the recrystallization of the crude synthesis product does not control for the polymorphic forms of 5-azacytidine. Specifically, the prior art recrystallization procedure produces either Form I substantially free of other forms, or a Form I/II mixed phase i.e. a solid material in which 5-azacytidine is present in a mixed phase of both polymorphic Form I and polymorphic Form II. Thus, the prior art procedures do not allow one to reliably target Form I as the single polymorphic form in the drug substance. The present invention provides methods that allow one to recrystallize 5-azacytidine as polymorphic Form I robustly and reproducibly.

SUMMARY OF THE INVENTION

The present invention provides methods for robustly and reproducibly isolating 5-azacytidine as polymorphic Form I substantially free of other forms. The methods involve recrystallizing dissolved 5-azacytidine from a primary solvent/co-solvent mixture and then collecting the resultant crystals. The invention also provides pharmaceutical compositions comprising Form I of 5-azacytidine together with a pharmaceutically acceptable excipient, diluent, or carrier.

DETAILED DESCRIPTION OF THE PREFERRED EMBODIMENTS

Polymorphic Form I of 5-azacytidine

Form I of 5-azacytidine is described fully in Ser. No. 10/390,578 (see supra), and such descriptions are incorporated by reference herein. Table I provides the most prominent 2θ angles, d-spacing and relative intensities for Form I observed using X-Ray Powder Diffraction (XRPD) performed according the method of Example 4:

TABLE 1

5-azacytidine Form I—the most prominent 2θ angles, d-spacing and relative intensities (Cu Kα radiation)

| 2θ Angle (°) | d-spacing (Å) | Relative Intensity |
|---|---|---|
| 12.182 | 7.260 | 39.1 |
| 13.024 | 6.792 | 44.1 |
| 14.399 | 6.146 | 31.5 |
| 16.470 | 5.378 | 27.1 |
| 18.627 | 4.760 | 16.0 |
| 19.049 | 4.655 | 35.9 |
| 20.182 | 4.396 | 37.0 |
| 21.329 | 4.162 | 12.4 |
| 23.033 | 3.858 | 100.0 |

TABLE 1-continued 5-azacytidine Form I—the most prominent 2θ angles, d-spacing and relative intensities (Cu Kα radiation)

| 2θ Angle (°) | d-spacing (Å) | Relative Intensity |
|---|---|---|
| 23.872 | 3.724 | 28.0 |
| 26.863 | 3.316 | 10.8 |
| 27.135 | 3.284 | 51.5 |
| 29.277 | 3.048 | 25.6 |
| 29.591 | 3.016 | 11.5 |
| 30.369 | 2.941 | 10.8 |
| 32.072 | 2.788 | 13.4 |

Isolation of Polymorphic Form I of 5-azacytidine by Recrystallization

Form I of 5-azacytidine may be reproducibly isolated substantially free of other forms by recrystallizing dissolved 5-azacytidine and collecting the resultant crystals. Specifically, 5-azacytidine is first dissolved completely in at least one suitable primary solvent, preferably a polar solvent, more preferably a polar aprotic solvent. Suitable polar aprotic solvents include, but are not limited to, dimethylformamide (DMF), dimethylacetamide (DMA), dimethylsulfoxide (DMSO), and N-methylpyrrolidinone (NMP). The most preferred polar aprotic solvent is DMSO. Mixtures of two or more primary solvents are also contemplated for dissolving the 5-azacytidine, for example a mixture of DMSO and DMF.

The 5-azacytidine used to form the solution may be synthesized by any procedure known in the art; an exemplary prior art synthesis scheme is provided in Example 1. Any polymorphic or pseudopolymorphic form(s) of 5-azacytidine, including mixed phases, may be used to form the solution. Amorphous 5-azacytidine may also be used to form the solution. It is preferred, but not required, that the primary solvent is preheated to an elevated temperature in order to ensure that the 5-azacytidine is dissolved completely. An especially preferred primary solvent is dimethyl sulfoxide, (DMSO), most preferably preheated to a temperature in the range of about 40° C. to about 90° C.

Following solvation of the 5-azacytidine in the primary solvent, at least one co-solvent is added to the solution of 5-azacytidine. Suitable co-solvents include $C_2$-$C_5$ alcohols (which term hereinafter refers to $C_2$-$C_5$ alcohols that are independently: branched or unbranched, substituted or unsubstituted), aliphatic ketones (which term hereinafter refers to aliphatic ketones that are independently: branched or unbranched, substituted or unsubstituted), and alkyl cyanides (which term hereinafter refers to alkyl cyanides that are independently: branched or unbranched, substituted or unsubstituted). Preferred $C_2$-$C_5$ alcohols, aliphatic ketones, and alkyl cyanides, along with other suitable solvents, are listed below as Class 2 (solvents to be limited) and Class 3 (solvents of low toxic potential) per the International Conference on Harmonization's (ICH) Guideline for Residual Solvents, July 1997). The use of mixtures of two or more of any of the aforementioned co-solvents is also included within the scope of the invention.

Class 2
Acetonitrile
Chlorobenzene
Cyclohexane
1,2-Dichloroethene
Dichloromethane
1,2-Dimethoxyethane
N,N-Dimethylformamide
N,N-Dimethyl acetamide
1,4-Dioxane
2-Ethoxyethanol
Ethyleneglycol
Formamide
2-Methoxyethanol
Methylbutyl ketone
Methylcyclohexane
Nitromethane
Pyridine
Sulfolane
Tetralin
1,1,2-Trichloroethene
Class 3
1-Butanol
1-Pentanol
1-Propanol
2-Butanol
2-Methyl-1-propanol
2-Propanol (isopropyl alcohol)
3-Methyl-1-butanol
Acetone
Anisole
Butyl acetate
Cumene
Ethanol
Ethyl acetate
Ethyl ether
Ethyl formate
Isobutyl acetate
Isopropyl acetate
Methyl acetate
Methylethyl ketone
Methylisobutyl ketone
Propyl acetate
tert-Butylmethyl ether
Tetrahydrofuran It is preferred, but not required, that the co-solvents are preheated before mixing with the primary solvent, preferably to a temperature below the temperature at which a substantial portion of the co-solvent would boil, most preferably to about 50° C. It is also preferred, but not required, that the co-solvent(s) is added gradually to the primary solvent(s).

Following mixing, the primary solvents)/co-solvent(s) mixture is then equilibrated at different temperatures in order to promote either a slow recrystallization or a fast recrystallization of Form I of 5-azacytidine, as described below.

By slow recrystallization is meant that the co-solvent/DMSO solution is allowed to equilibrate at a temperature in the range from about 0° C. to about 40° C., preferably in the range of about 15° C. to about 30° C., and most preferably at about ambient temperature. Slow recrystallization of Form I of 5-azacytidine is preferably performed using $C_2$-$C_5$ alcohols, aliphatic ketones, or alkyl cyanides as the co-solvent. More preferably, slow recrystallization is performed with Class 3 $C_2$-$C_5$ alcohols, Class 3 aliphatic ketones, or acetonitrile (Class 2). The most preferred Class 3 $C_2$-$C_5$ alcohols are ethanol, isopropyl alcohol, and 1-propanol, and the most preferred Class 3 aliphatic ketone is methylethyl ketone.

By fast recrystallization is meant that the co-solvent solution is allowed to equilibrate at a temperature of below 0° C., preferably below about −10° C., and most preferably at about −20° C. Fast recrystallization of Form I of 5-azacytidine is preferably performed with a $C_3$-$C_5$ alcohol (which term hereinafter refers to $C_3$-$C_5$ alcohols which are independently: branched or unbranched, substituted or unsubstituted) or an alkyl cyanide as the co-solvent. More preferably the $C_3$-$C_5$ alcohol is a Class 3 solvent, and the alkyl cyanide is acetonitrile. The most preferred Class 3 $C_3$-$C_5$ alcohols are isopropyl alcohol (2-propanol) and 1-propanol.

Non-limiting examples of protocols for the recrystallization of Form I according to the methods described herein are provided in Examples 2 (slow recrystallization with DMSO as the primary solvent and ethanol, isopropyl alcohol, acetonitrile, or methylethyl ketone as the co-solvent) and 3 (fast recrystallization with DMSO as the primary solvent, and isopropyl alcohol or acetonitrile as the co-solvent) below.

Following recrystallization, the Form I of 5-azacytidine crystals may be isolated from the co-solvent mixture by any suitable method known in the art. Preferably, the Form I crystals are isolated using vacuum filtration through a suitable filter medium or by centrifugation.

Using the novel methods provided herein, it is possible for the first time to target Form I of 5-azacytidine as the drug substance reproducibly and robustly. In particular, isopropyl alcohol and acetonitrile reliably produce Form I independent of cooling rate (either slow recrystallization or fast recrystallization) and are preferred as the recrystallization co-solvents to recover Form I. Most preferably, Form I is isolated using isopropyl alcohol as the co-solvent since isopropyl alcohol carries a Class 3 risk classification (solvent of low toxic potential), whereas acetonitrile carries a Class 2 risk classification (solvent to be limited). The use of the DMSO/isopropyl alcohol system allows Form I of 5-azacytidine to be reliably recovered for the first time from solvents of low toxic potential without requiring control over the rate of recrystallation. In the most preferred embodiment, Form I of 5-azacytidine may be recovered simply by dissolving 5-azacytidine in DMSO (preferably heated to a temperature in the range of about 40° C. to about 90° C. prior to the addition of 5-azacytidine), adding isopropyl alcohol, and allowing the resulting solvent mixture to equilibrate at about ambient temperature.

In some embodiments of the invention, Form I of 5-azacytidine may be recovered from a primary solvent(s)/co-solvent(s) mixture by "seeding" with a small amount of Form I of 5-azacytidine either prior to, or during, the addition of the co-solvent(s). By seeding with Form I, it is possible to expand the list of suitable co-solvents and co-solvent classes beyond those listed above. For example, it is known that recrystallization from the DMSO/methanol system produces either Faun I, or a Form I/II mixed phase (see Example 1). If a small amount of Form I is added to the solution of 5-azacytidine in DMSO prior to addition of the methanol co-solvent, or is added during the addition of the methanol co-solvent, then Form I of 5-azacytidine may be reliably isolated.

By allowing the isolation of a single polymorphic form, one skilled in the art will appreciate that the present invention allows for the first time the production of 5-azacytidine drug substance with uniform and consistent properties from batch to batch, which properties include but are not limited to solubility and dissolution rate. In turn, this allows one to provide 5-azacytidine drug product (see below) which also has uniform and consistent properties from batch to batch.

Pharmaceutical Formulations

For the most effective administration of drug substance of the present invention, it is preferred to prepare a pharmaceutical formulation (also known as the "drug product" or "pharmaceutical composition") preferably in unit dose form, comprising one or more of the 5-azacytidine polymorphs of the present invention and one or more pharmaceutically acceptable carrier, diluent, or excipient. Most preferably, Form I 5-azacytidine prepared according to the methods provided herein is used to prepare the pharmaceutical formulation.

Such pharmaceutical formulation may, without being limited by the teachings set forth herein, include a solid form of the present invention which is blended with at least one pharmaceutically acceptable excipient, diluted by an excipient or enclosed within such a carrier that can be in the form of a capsule, sachet, tablet, buccal, lozenge, paper, or other container. When the excipient serves as a diluent, it may be a solid, semi-solid, or liquid material which acts as a vehicle, carrier, or medium for the 5-azacytidine polymorph(s). Thus, the formulations can be in the form of tablets, pills, powders, elixirs, suspensions, emulsions, solutions, syrups, capsules (such as, for example, soft and hard gelatin capsules), suppositories, sterile injectable solutions, and sterile packaged powders.

Examples of suitable excipients include, but are not limited to, starches, gum arabic, calcium silicate, microcrystalline cellulose, polyvinylpyrrolidone, cellulose, water, syrup, and methyl cellulose. The formulations can additionally include lubricating agents such as, for example, talc, magnesium stearate and mineral oil; wetting agents; emulsifying and suspending agents; preserving agents such as methyl- and propyl-hydroxybenzoates; sweetening agents; or flavoring agents. Polyols, buffers, and inert fillers may also be used. Examples of polyols include, but are not limited to: mannitol, sorbitol, xylitol, sucrose, maltose, glucose, lactose, dextrose, and the like. Suitable buffers encompass, but are not limited to, phosphate, citrate, tartrate, succinate, and the like. Other inert fillers which may be used encompass those which are known in the art and are useful in the manufacture of various dosage forms. If desired, the solid pharmaceutical compositions may include other components such as bulling agents and/or granulating agents, and the like. The compositions of the invention can be formulated so as to provide quick, sustained, controlled, or delayed release of the drug substance after administration to the patient by employing procedures well known in the art.

In certain embodiments of the invention, the 5-azacytidine polymorph(s) may made into the form of dosage units for oral administration. The 5-azacytidine polymorph(s) may be mixed with a solid, pulverant carrier such as, for example, lactose, saccharose, sorbitol, mannitol, starch, amylopectin, cellulose derivatives or gelatin, as well as with an antifriction agent such as for example, magnesium stearate, calcium stearate, and polyethylene glycol waxes. The mixture is then pressed into tablets or filled into capsules. If coated tablets, capsules, or pulvules are desired, such tablets, capsules, or pulvules may be coated with a concentrated solution of sugar, which may contain gum arabic, gelatin, talc, titanium dioxide, or with a lacquer dissolved in the volatile organic solvent or mixture of solvents. To this coating, various dyes may be added in order to distinguish among tablets with different active compounds or with different amounts of the active compound present.

Soft gelatin capsules may be prepared in which capsules contain a mixture of the 5-azacytidine polymorph(s) and vegetable oil or non-aqueous, water miscible materials such as, for example, polyethylene glycol and the like. Hard gelatin capsules may contain granules or powder of the 5-azacytidine polymorph in combination with a solid, pulverulent carrier, such as, for example, lactose, saccharose, sorbitol, mannitol, potato starch, corn starch, amylopectin, cellulose derivatives, or gelatin.

Tablets for oral use are typically prepared in the following manner, although other techniques may be employed. The solid substances are gently ground or sieved to a desired particle size, and a binding agent is homogenized and suspended in a suitable solvent. The 5-azacytidine polymorph(s)

and auxiliary agents are mixed with the binding agent solution. The resulting mixture is moistened to form a uniform suspension. The moistening typically causes the particles to aggregate slightly, and the resulting mass is gently pressed through a stainless steel sieve having a desired size. The layers of the mixture are then dried in controlled drying units for a pre-determined length of time to achieve a desired particle size and consistency. The granules of the dried mixture are gently sieved to remove any powder. To this mixture, disintegrating, anti-friction, and anti-adhesive agents are added. Finally, the mixture is pressed into tablets using a machine with the appropriate punches and dies to obtain the desired tablet size.

In the event that the above formulations are to be used for parenteral administration, such a formulation typically comprises sterile, aqueous and non-aqueous injection solutions comprising one or more 5-azacytidine polymorphs for which preparations are preferably isotonic with the blood of the intended recipient. These preparations may contain anti-oxidants, buffers, bacteriostats, and solute; which render the formulation isotonic with the blood of the intended recipient. Aqueous and non-aqueous suspensions may include suspending agents and thickening agents. The formulations may be present in unit-dose or multi-dose containers, for example, sealed ampules and vials. Extemporaneous injection solutions and suspensions may be prepared from sterile powders, granules, and tablets of the kind previously described.

Liquid preparations for oral administration are prepared in the form of solutions, syrups, or suspensions with the latter two forms containing, for example, 5-azacytidine polymorph(s), sugar, and a mixture of ethanol, water, glycerol, and propylene glycol. If desired, such liquid preparations contain coloring agents, flavoring agents, and saccharin. Thickening agents such as carboxymethylcellulose may also be used.

As such, the pharmaceutical formulations of the present invention are preferably prepared in a unit dosage form, each dosage unit containing from about 5 mg to about 200 mg, more usually about 100 mg of the 5-azacytidine polymorph(s). In liquid form, dosage unit contains from about 5 to about 200 mg, more usually about 100 mg of the 5-azacytidine polymorph(s). The term "unit dosage form" refers to physically discrete units suitable as unitary dosages for human subjects/patients or other mammals, each unit containing a predetermined quantity of the 5-azacytidine polymorph calculated to produce the desired therapeutic effect, in association with preferably, at least one pharmaceutically acceptable carrier, diluent, or excipient.

The following examples are provided for illustrative purposes only, and are not to be construed as limiting the scope of the claims in any way.

EXAMPLES

Example 1

Prior Art Procedure for Synthesis and Recrystallization of 5-azacytidine Drug Substance 5-azacytidine may be synthesized using commercially available 5-azacytosine and 1,2,3,5-tetra-O-acetyl-β-D-ribofuranose (RTA) according to the following pathway:

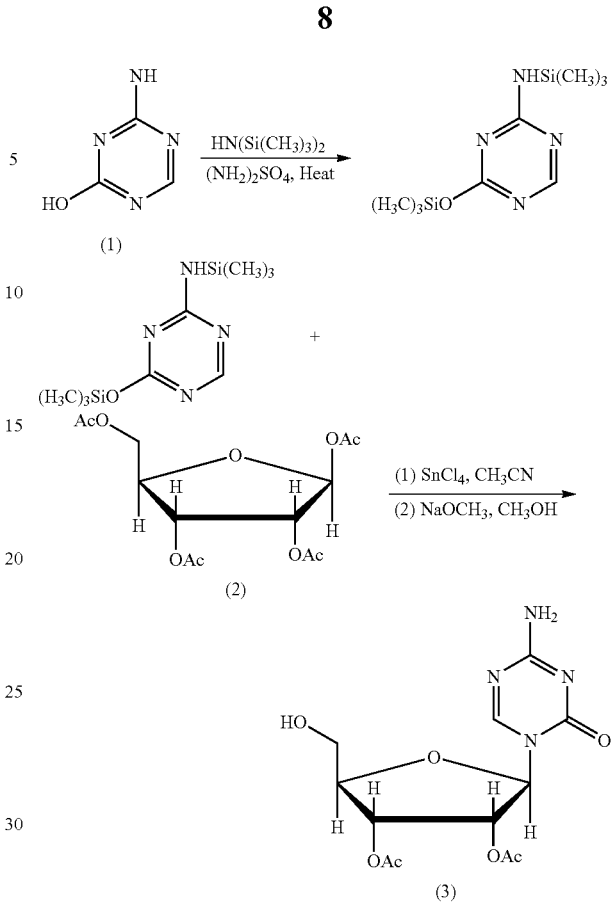

The crude synthesis product is dissolved in DMSO (preheated to about 90° C.), and then methanol is added to the DMSO solution. The co-solvent mixture is equilibrated at approximately −20° C. to allow 5-azacytidine crystal formation. The product is collected by vacuum filtration and allowed to air dry.

Example 2

Form I of 5-azacytidine: Slow Recrystallization of 5-azacytidine from Co-Solvent Systems Approximately 250 mg of 5-azacytidine was dissolved with approximately 5 ml of dimethyl sulfoxide (DMSO), preheated to approximately 90° C., in separate 100-mL beakers. The solids were allowed to dissolve to a clear solution. Approximately 45 mL of ethanol, isopropyl alcohol, acetonitrile, or methyl ethyl ketone co-solvent, preheated to approximately 50° C., was added to the solution and the resultant solution was mixed. The solution was covered and allowed to equilibrate at ambient conditions. The product was collected by vacuum filtration using a Buchner funnel.

Example 3

Form I of 5-azacytidine: Fast Recrystallization of 5-azacytidine from Co-Solvent Systems Approximately 250 mg of 5-azacytidine was dissolved with approximately 5 mL of DMSO, preheated to approximately 90° C., in separate 100-ml beakers. The solids were allowed to dissolve to a clear solution. Approximately 45 mL of isopropyl alcohol or acetonitrile co-solvent, preheated to approximately 50° C., was added to the solution and the resultant solution was mixed. The solution was covered and placed in a freezer to equilibrate at approximately −20° C. to allow crystal formation. Solutions were removed from the freezer after crystal formation. The product was collected by vacuum filtration using a Buchner funnel.

Example 4

X-Ray Powder Diffraction of Recrystallized 5-azacytidine

X-ray powder diffraction (XRPD) patterns for each sample were obtained on a Scintag XDS 2000 or a Scintag $X_2$ θ/θ diffractometer operating with copper radiation at 45 kV and 40 mA using a Kevex Psi Peltier-cooled silicon detector or a Thermo ARL Peltier-cooled solid state detector. Source slits of 2 or 4 mm and detector slits of 0.5 or 0.3 mm were used for data collection. Recrystallized material was gently milled for approximately one minute using an agate mortar and pestle. Samples were placed in a stainless steel or silicon sample holder and leveled using a glass microscope slide. Powder diffraction patterns of the samples were obtained from 2 to 42° 2θ at 1°/minute. Calibration of the $X_2$ diffractometer is verified annually using a silicon powder standard.

XRPD performed according to this method revealed that the Form I of 5-azacytidine was isolated in Example 2 by slow recrystallization using either ethanol, isopropyl alcohol, acetonitrile, or methyl ethyl ketone as the co-solvent, and in Example 3 by fast recrystallization using isopropyl alcohol or acetonitrile as the co-solvent. The results indicate that Form I of 5-azacytidine may be reliably recovered from the DMSO/isopropyl alcohol and DMSO/acetonitrile solvent systems without control of the rate of recrystallization.

What is claimed is:

1. A method for isolating crystalline Form I of 5-azacytidine substantially free of other forms, the method comprising:
   recrystallizing 5-azacytidine from a solvent mixture comprising at least one polar aprotic solvent and at least one co-solvent selected from the group consisting of:
   1,1,2-trichloroethene,
   1,2-dichloroethene,
   1,2-dimethoxyethane,
   1,4-dioxane,
   1-butanol,
   1-pentanol,
   1-propanol,
   2-butanol,
   2-ethoxyethanol,
   2-methoxyethanol,
   2-methyl-1-propanol,
   2-propanol,
   3-methyl-1-butanol,
   acetone,
   acetonitrile,
   anisole,
   butyl acetate,
   chlorobenzene,
   cumene,
   cyclohexane,
   dichloromethane,
   ethyl acetate,
   ethyl ether,
   ethyl formate,
   ethyleneglycol,
   formamide,
   isobutyl acetate,
   isopropyl acetate,
   methyl acetate,
   methylbutyl ketone,
   methylcyclohexane,
   methylisobutyl ketone,
   N,N-dimethylacetamide,
   N,N-dimethylformamide,
   nitromethane,
   propyl acetate,
   pyridine,
   sulfolane,
   tert-butylmethyl ether,
   tetrahydrofuran, and
   tetralin,
   by cooling the solvent mixture from a temperature at which the 5-azacytidine dissolves completely to about −20° C.; and
   isolating the recrystallized 5-azacytidine.

2. The method of claim 1, wherein said polar aprotic solvent is selected from the group consisting of dimethylsulfoxide, dimethylformamide, dimethylacetamide, and N-methylpyrrolidinone.

3. The method of claim 1, wherein said polar aprotic solvent is dimethylsulfoxide.

4. The method of claim 1, wherein said co-solvent is acetonitrile.

5. The method of claim 1, wherein said co-solvent is 2-propanol.

6. The method of claim 1, wherein said co-solvent is 1-propanol.

7. The method of claim 2, wherein said co-solvent is acetonitrile.

8. The method of claim 2, wherein said co-solvent is 2-propanol.

9. The method of claim 2, wherein said co-solvent is 1-propanol.

10. The method of claim 3, wherein said co-solvent is acetonitrile.

11. The method of claim 3, wherein said co-solvent is 2-propanol.

12. The method of claim 3, wherein said co-solvent is 1-propanol.

* * * * *